United States Patent
Olivier-Terras

Patent Number: 5,554,374
Date of Patent: Sep. 10, 1996

[54] SKIN PREPARATION USING NANOSPHERES

[75] Inventor: Josette Olivier-Terras, Peronnas, France

[73] Assignee: Cosmetics Development Company Limited, United Kingdom

[21] Appl. No.: 256,634

[22] Filed: Oct. 17, 1994

[30] Foreign Application Priority Data

Jan. 16, 1992 [FR] France ................... 92 00619

[51] Int. Cl.$^6$ ....................... A61K 7/48
[52] U.S. Cl. ............. 424/401; 424/59; 424/60; 424/450; 424/491; 514/844
[58] Field of Search ............ 424/401, 59, 60, 424/491, 450; 514/844

[56] References Cited

U.S. PATENT DOCUMENTS 5,034,228  7/1991  Meybeck et al. .............. 424/401

FOREIGN PATENT DOCUMENTS 0381543  8/1990  European Pat. Off. .
0447318  9/1991  European Pat. Off. .
2591105  6/1987  France .
2664164  1/1992  France .

OTHER PUBLICATIONS

Harry Cosmeticology by Ralph Harry pp. 307–321 (1974).
"Production And Identification of Liposomes, Sphingosomes and Nanoparticles"; Brunke et al 5 Sep. 1991 (pp. 514–517).
"A New System of Encapsulation: Collagen Glycosaminoglycans Based Capsules"; A. Huc et al.—27 Mar. 1991 (pp. 180–186).

*Primary Examiner*—Jyothsna Venkat
*Attorney, Agent, or Firm*—Harness, Dickey & Pierce, P.L.C.

[57] ABSTRACT

Preparation for skin use comprising excipients, a drug carrier encapsulating beta-carotene and a blend of UV-A and UV-B sun filters characterized in that: the drug carrier consisting of nanospheres represents 3 to 6% by weight of the preparation; the proportion of UV-B filters is greater than that of the UV-A filters; and the UV-B filters have a cinnamic structure. Application in the treatment of melanic skin stains.

6 Claims, No Drawings

SKIN PREPARATION USING NANOSPHERES

The invention relates to a new preparation for use on the skin, composed of a mixture of excipients, sunscreen agents and drug carriers, intended for attenuating or delaying the appearance of melanin spots on the skin.

As is known, the expression "drug carriers" denotes small-sized hollow molecules which form reservoirs for active products, which are thus protected and which may be liberated or released at the appropriate time at the most suitable site (bioavailability). Liposomes, described, for example, in the document FR-A-2,315,991 corresponding to the document U.S. Pat. No. 4,217,344, are the best known of these carriers.

Drug carriers encapsulating beta-carotene are known for their action on cutaneous hyperpigmentations of melanotic origin, in particular light-induced melanin spots, chloasmas, melasmas, iatrogenic pigmentations or cosmetic pigmentations enhanced by sunlight, and friction pigmentations. However, this action is rather lengthy, often partial or even haphazard.

In the document FR-A-2,591,105 corresponding to the doument U.S. Pat. No. 5,034,228, a preparation was described for use on the skin, based on liposomes containing as active agent a carotenoid, such as a carotenoid, in particular, beta-carotene. In a practical embodiment (Examples 5 and 6), the liposome suspension also contains a UV-A+B screening agent (no further details being given). This preparation is used for the treatment of solar elastosis and skin regeneration, or as a cicatrizing agent. Unfortunately this type of preparation has hardly been developed, doubtless as a result:

on the one hand, of the appreciable size of liposomes which, for some skin applications, limit the penetration of the preparation into the cellular interstices, in particular between the corneocytes;

on the other hand, of the in vitro and in vivo instability of liposomes over time, which can cause untimely releases of the encapsulated beta-carotene, which will then react as a tissue pigment and thus cause the appearance of spots on the skin.

The invention overcomes these drawbacks. It relates to an improved preparation of the type in question, which gives excellent results from the standpoint of depigmentation, and which is easy to manufacture, stable, cheap, more effective and does not display untimely release effects.

This preparation for use on the skin comprising excipients, a drug carrier encapsulating beta-carotene and a mixture of UV-A and UV-B sunscreen agents, is characterized:

in that the drug carrier, consisting of nanospheres encapsulating beta-carotene, represents from 3 to 6% of the weight of the preparation;

in that the proportion of UV-B screening agents is higher than those of the UV-A screening agents;

and in that UV-B screening agent is a cinnamic derivative.

"Nanospheres" denote drug carriers composed of a nanometer-sized, generally spherical particles encapsulating a particular substance, in this instance beta-carotene. These compounds are amptly described in the literature.

In other words, the invention lies in a threefold selection, namely, in the first place, the selection of a specific carrier, namely nanospheres encapsulating beta-carotene, and then the selection of a proportion of UV-B screening agents higher than that of UV-A screening agents, and lastly the selection of a specific type of UV-B screening agent, namely cinnamic derivatives. There was no reason to suppose that this threefold selection would enable the drawbacks of the preparations known hitherto, in particular those described in the document FR-A-2,591,105 referred to in the preamble, to be overcome successfully, namely a better penetration into the skin and a better bioavailability as a result of the small size of the nanospheres, a better efficacy as a result of the ratio of the screening agents, and lastly a synergy which possesses an inhibitory effect on tyrosinase as a result of the cinnamic nature of the UV-B screening agents.

The choice of a higher proportion of UV-B screening agents from that of UV-A screening agents runs counter to the usual teachings. In effect, it is known that UV-A screening agents are supposed to stop UV-A radiation, which acts essentially on the dermis and beyond. On the other hand, it is known that UV-B screening agents block UV-B radiation, which reaches only the epidermis and stops at the level of the basal layer of the epidermis. Accordingly, in a preparation intended for combatting hyperpigmentations of melanotic origin, it is sought above all to prevent the UV rays from reaching the melanocytes and exciting them, and thus triggering their production of melanin. Now, it is known that the melanocytes lie at the dermo-epidermal junction, and hence in a region which is markedly more subjected to the action of UV-A radiation than to that of UV-B radiation which has difficulty in reaching this region. Accordingly, to protect the melanocytes and avoid or reduce their excitation by UV radiation, it was customary to employ UV-A screening agents, either alone or in combination with a small proportion of UV-B screening agents.

Now, it turns out that, in the case arising here, to obtain optimal efficacy, it is necessary to use a mixture of UV-A screening agents and UV-B screening agents, but one in which the proportion of UV-B screening agents is higher than that of UV-A screening agents.

This paradoxical effect, which is surprising with respect to the earlier teachings, may originate from two causes.

In the first place, since the melanocytes are essentially localized at the dermo-epidermal junction, they are initially activated by UV-A radiation. Once activated, the organelles of these melanocytes start to migrate, which leads them to the epidermal region between the keratinocytes where they are then subjected to the action of UV-B radiation which excites them and stimulates melanin production. For all these reasons, it is essential to have a large proportion of UV-B screening agents.

According to another feature of the invention, these UV-B screening agents have to be cinnamic derivatives. As cinnamic derivatives capable of being used for this application, there may be mentioned:

potassium cinnamate, propyl 4-methoxycinnamate, amyl or 2-ethylcetyl 4-methoxycinnamate, alpha-cyano-4-methoxycinnamic acid or its esters, cyclohexyl 4-methoxycinnamate, 4-methoxycinnamic acid in the form of its potassium, sodium or diethanolamine salts.

The preferred UV-B screening compound is octyl methoxycinnamate.

Advantageously, in practice:

the nanospheres are hollow spheres comprising a collagen and glycosaminoglycan membrane, such as those marketed by COLETICA under the trademark NANOCOLLASPHERES and NANOTHALASPHERES: these nanospheres are described in the document FR-A-89/01221; this type of carrier has the advantage, in combination with excipients and the characteristic mixture of screening agents, of giving skin preparations which are less irritant, completely biodegradable and biocompatible and which display controlled release:

the nanospheres loaded with beta-carotene represent from 3 to 6% of the weight of the preparation, and preferably in the vicinity of 4%; in effect, it has been observed that if the proportion of nanospheres is lower than 3%, practically no effect on pigmentation is obtained, and that, on the other hand, if this proportion exceeds 6%, there is a risk of the beta-carotene behaving as a tissue pigment; as already stated, the best results are obtained with a proportion in the region of 4%;

the mixture of UV-A screening agents and UV-B screening agents must be greater than 4% and less than 15% of the weight of the proportion; in effect, it has been observed that if this proportion of sunscreen agents is lower than 4%, a significant preventative effect is no longer obtained, and that if this proportion exceeds 15%, the statutory accepted levels are frequently exceeded, with not insignificant risks of skin irritation and allergies.

The preparation also contains excipients in common use for such a skin application. It is preferable to use oils containing unsaturated fatty acids which are well known for preventing skin ageing, such as borage oils or wheat-gem oils. These excipients must not affect the stability of the nanoparticles or react with the sunscreen agents. It is hence preferable for the proportion of fats to be as small as possible, and in particular smaller than one half or even than one third. Commonly, the mixture of excipients can also contain antioxidants and/or preservatives which are known for such an application.

In a practial embodiment, the preparation according to the invention contains:

4% of nanospheres encapsulating beta-carotene,

4% of octyl methoxycinnamate (UV-B screening agent),

3% of butyl methoxy dibenzoylmethane (UV-A screening agent),

1% of preservative, 0.1% of an ion-chelating agent, 0.3% of a gelling agent based on modified cellulose, 0.6% of an agent intended for adjusting the pH, the remainder to 100% consisting of demineralized water and a mixture of excipients in common use for a skin application.

It is self-evident that, in the preparation according to the invention, it is essential that the nanospheres encapsulating beta-carotene, the sunscreen agents and the excipients do not react with one another. When the mixing of these components is carried out, the appearance of an orange coloration is sometimes observed. It is thought that this may originate from a reaction of the UV-A screening agents with traces of metals resulting from impurities contained in the other products. This drawback is overcome by then adding an ion-chelating agent.

Generally, the finished preparation is very light in colour, or even pale yellow, depending on the quality of the oils employed. This preparation is creamy, smooth and easy to spread, and is readily stored at room temperature, in particular in an air-free tube, even for longer than one year.

This skin preparation is readily applied to the hand, in particular on the back of the hand, and penetrates rapidly under the effect of a gentle massage.

Good results are obtained by applying this preparation twice daily for one to five months, or even continuously.

Once the preparation has been placed on the skin, the sunscreen agents stop the UV radiation. As a result, the melanocytes are no longer excited and no longer manufacture melanin, the abnormalities of production of which, as is known, may be the source of cutaneous hyperpigmentations.

Simultaneously, the nanospheres encapsulating beta-carotene enter the stratum corneum and come into contact with the membrane of the melanocytes. These two membranes then fuse, causing the beta-carotene to pass into the cytoplasm of the melanocyte where it saturates the proteins that specifically transport carotenoids, and/or the nuclear receptor sites. There follows a cessation of melanogenesis, resulting in a cessation of pigment production and consequently a cessation of the appearance of new spots and of the intensification of existing spots. Concomitantly, the cinnamic derivative, chosen, moreover, for its UV-B screening properties, can interfere in melanogenesis as a tyrosinase inhibitor, and by this mechanism, different from that elaborated above, slow down or even stop melanin production through its intrinsic action. As a result of the natural elimination of melanin, the spots abate and then disappear almost completely in a period of three weeks to five months, which it was not possible to obtain hitherto.

The manner in which the invention may be carried out, and the advantages deriving therefrom, will be more clearly apparent from the examples of implementation which follow:

EXAMPLE 1

At room temperature and with gentle stirring, the following are mixed, respectively, in 220 grams (22%) of demineralized water:

3 grams (0.30%) of a gelling agent based on modified cellulose, marketed by GOODRICH under the brand name "CARBOPOL 934";

40 grams (4%) of nanospheres encapsulating beta-carotene, which take the form of an aqueous suspension having beta-carotene concentrations of 0.5%, marketed by COLETICA under the brand name "NANOTHALASPERES" and the membrane of which is made of collagen and glycosaminoglycan; these nanospheres are presented in the form of microcapsules less than one (1) micrometer in diameter, characterized in that they comprise a mixed wall of marine collagen or atelocollagen and crosslinked glycosaminoglycans, it being possible for the proportion of glycosaminoglycans relative to marine collagen or atelocollagen to vary from 15% to 50% by weight; the glycosaminoglycans are chosen from the group consisting of chondroitin 4-sulphate, chondroitin 6-sulphate, dermatan sulphate, heparin sulphate, keratan sulphate and heparin and its derivatives;

10 grams (1%) of a liquid preservative based on propylene glycol, diazolidinylurea, methylparaben and propylparaben, marketed by SUTTON under the brand name "GERMABEN II";

1 gram (0.1%) of an ion-chelating agent known under the name disodium EDTA.

These ingredients are stirred slowly at room temperature until a thoroughly homogeneous mixture is obtained.

Separately, with rapid stirring (1,000 rpm) and at 80° C., the following are mixed in order:

40 grams (4%) of a UV-B sunscreen agent based on octyl methoxycinnamate, marketed by GIVAUDAN under the brand name "PARSOL MCX";

30 grams (3%) of a UV-A sunscreen agent based on butylmethoxydibenzoylmethane, marketed by GIVAUDAN under the brand name "PARSOL 1789";

10 grams (14) of an excipient based on cetyl alcohol;

90 grams (94) of another excipient based on 2-octyldodecyl myristate;

80 grams (8%) of an excipient based on a nonionic derivative of white beeswax, marketed by GATTEFOSSE under the brand name "APIFIL";

10 grams (1%) of an excipient based on borage oil;

30 grams (3%) of an excipient based on wheat-germ oil;

80 grams (8%) of an excipient based on isostearyl isostearate.

The mixture is stirred rapidly until perfect homogenization is obtained.

Demineralized water heated to 82° C. is then added to this latter mixture to the extent of 346.5 grams (34.65%). To initiate emulsion formation, the mixture is stirred rapidly while this water is poured into it.

When the emulsion has been formed and the temperature has dropped to 30°–35° C., the first phase containing the nanospheres of beta-carotene is then added, and 6 grams (0.6%) of a 50% solution of triethanolamine are added thereafter to adjust the pH, followed by 3 grams (0.3%) of a perfume and lastly 0.5 gram (0.05%) of an antioxidant marketed by GATTEFOSSE under the reference "WL 774".

The whole is mixed slowly at 30°–35° C.

The preparation obtained is a semi-liquid, creamy, smooth oil-in-water type emulsion which is light yellow-white in colour (depending on the quality of the oils used), the pH of which is between 6.8 and 7.5. Its distinctive odour is that associated with the perfume used.

This preparation, which is stable over time (no untimely release after one year of storage), may be applied to the skin at the rate of two applications daily for an unlimited period.

Sometimes from the third week onwards, and more generally within the five months following the start of application, a decrease is obtained in the intensity of the pigmented spots, or even their complete disappearance. Complete depigmentation is observed at between 7 and 11 weeks in 75% of cases treated.

Furthermore, the application of this cream prevents the appearance of new spots.

EXAMPLE 2

Example 1 is repeated, omitting the sunscreen agents.

On applying skin preparation under the same conditions, it is found that solar radiation then excites the melanocytes, leading to a rise in skin pigments.

The disappearance of the spots is only partial, is less obvious and takes longer.

EXAMPLE 3

Example 1 is repeated, omitting the nanosphere encapsulating beta-carotene. No effect is observed.

EXAMPLE 4

Example 1 is repeated, replacing the nanospheres by commercial liposomes encapsulating beta-carotene.

An emulsion is obtained having substantially the same appearance and the same physical properties as in Example 1. However, complete depigmentation at between 7 and 11 weeks is observed in only one half of the cases (against 75%).

EXAMPLE 5

Example 1 is repeated, reversing the proportion of sunscreen agents, namely 4% of UV-A and 3% of UV-B.

The disappearance of the spots is less obvious, and is obtained after a longer time.

EXAMPLE 6

Example 1 is repeated, replacing the UV-B screening agent of brand name "PARSOL MCX" by another UV-B sunscreen agent based on propyl 4-methoxycinnamte.

Results similar to those obtained in Example 1 are obtained.

These examples show clearly the synergistic effect resulting from the combination of nanospheres encapsulating beta-carotene and UV-A and UV-B sunscreen agents.

Accordingly, these skin preparations may be used successfully on patients displaying cutaneous hyperpigmentations of melanotic origin: light-induced melanin spots, chloasmas, melasmas, iatrogenic pigmentations or cosmetic pigmentations enhanced by sunlight, friction pigmentations, and the like.

I claim:

1. In a skin preparation comprising excipients, a drug carrier encapsulating beta-carotene and a mixture of UV-A and UV-B sunscreen agents, the improvement consisting:

in that the drug carrier consists of nanospheres, and represents from 3 to 6% of the weight of the preparation;

the proportion of UV-B screening agents is higher than those of the UV-A screening agents;

and the UV-B screening agents, are selected from the group consisting of octyl methoxycinnamate, potassium cinnamate, propyl 4-methoxycinnamate, 2-ethylcetyl 4-methoxycinnamate, amyl 4-methoxycinnamate, alpha-cyano 4-methoxycinnamic acid, cyclohexyl 4-methoxycinnamate and potassium, sodium, or diethanolamine salts of 4-methoxycinnamic acid.

2. A skin preparation according to claim 1, characterised in that the nanospheres are in the form of spherical particles encapsulating beta-carotene having a collagen and glycosaminoglycan membrane.

3. A skin preparation according to either of claims 1 and 2, characterised in that the UV-A and UV-B screening agents represent 4 to 15% of the weight of the preparation.

4. A skin preparation according to claim 1, characterised in that the UV-B screening agent is octyl methoxycinnamate.

5. A skin preparation according to one of claims 1 to 4, characterised in that the excipients contain a mixture of fatty acid oils, antioxidants and preservatives.

6. In a skin preparation comprising excipient, drug carriers encapsulating beta-carotene and a mixture of UV-A and UV-B screening agents, the improvement consisting of, per one hundred parts:

3 to 6%, of nanospheres encapsulating beta-carotene;

4% of octyl methoxycinnamate (UV-B screening agent),

3% of butylmethoxydibenzoylmethane (UV-A screening agent),

1% of preservative, 0.1% of an ion-chelating agent, 0.3% of a gelling agent based on modified cellulose, 0.6% of an agent for adjusting the pH, the remainder to 100% consisting of demineralised water.

\* \* \* \* \*

UNITED STATES PATENT AND TRADEMARK OFFICE
CERTIFICATE OF CORRECTION

PATENT NO. : 5,554,374
DATED : September 10, 1996
INVENTOR(S) : Josette Olivier-Terras It is certified that error appears in the above-indentified patent and that said Letters Patent is hereby corrected as shown below:

On the Title Page under [22], "Filed: Oct. 17, 1994" should be --PCT Filed: Jan. 6, 1993--.

On the Title Page, following [22], insert the following headings and related information:
   --[86] PCT No.: PCT/FR93/00006--
   --§371 Date:   Oct. 17, 1994--
   --§102(e) Date: Oct. 17, 1994--
   --[87] PCT Pub. No.: WO93/13742--
   --   PCT Pub. Date: Jul. 22, 1993--

Column 3, line 24, "wheat-gem" should be --wheat-germ--.

Column 5, line 1, "(14)" should be --(1%)--.

Column 5, line 2, "(94)" should be --(9%)--.

Signed and Sealed this

Tenth Day of December, 1996

Attest:

BRUCE LEHMAN

*Attesting Officer*      *Commissioner of Patents and Trademarks*